United States Patent [19]

Shudo

[11] Patent Number: 4,723,028

[45] Date of Patent: Feb. 2, 1988

[54] STILBENE DERIVATIVES

[76] Inventor: Koichi Shudo, 2-25, 6-102, Higashiyama, Meguroku, Tokyo, Japan

[21] Appl. No.: 753,037

[22] Filed: Jul. 8, 1985

[30] Foreign Application Priority Data

Jul. 7, 1984 [JP] Japan .................... 59-141193

[51] Int. Cl.$^4$ ............................ C07C 69/76
[52] U.S. Cl. ........................ 560/8; 560/104; 562/405; 562/495; 514/544; 514/568; 514/569
[58] Field of Search ............... 560/104, 8; 562/405, 562/495; 514/544, 568, 569

[56] References Cited

FOREIGN PATENT DOCUMENTS 2854354  7/1979  Fed. Rep. of Germany .

OTHER PUBLICATIONS

Chemica Therapeutica, Jan.–Feb., 1980-15, No. 1, pp. 9-15; "Arotinoids, A New Class of Highly Active Retinoids", by Peter Loeliger, et al.

Breitman T. R., et al., Induction of Differentiation of the Human Promyelocytic Leukemia Cell Line (HL-60) by Retinoic Acid, Proc. Natl. Acad. Sci., 77, 2936-2940, (1980).

Moon, R. C. et al., Inhibition of Carcinogenesis by Retinoids, Cancer Research Suppl., 43, 2469s-2475s, (1983).

Pawson, et al., Retinoids at the Threshold: Their Biological Significance and Therapeutic Potential, J. Med. Chem., 25, 1269, 1277, (1982).

Mayer, et al., Retinoids, a New Class of Compounds with Prophylactic and Therapeutic Activities in Oncology and Dermatology, Experientia, 34, 1105-1119, (1978).

Koeffler P., Induction of Differentiation of Human Acute Myelogenous Leukemia Cells: Therapeutic Implications, J. Am. Soc. Hematology, 62, 709-721, (1983).

Primary Examiner—Paul J. Killos
Attorney, Agent, or Firm—Gordon W. Hueschen

[57] ABSTRACT

The application discloses certain stilbene compounds, pharmaceutical compositions thereof, method of treating thereof, method of diagnosis therewith, and method for the preparation thereof. The compounds and compositions are useful for diagnosis of leukemia types, the treatment of dermatological disorders, and as differentiation-inducing agents for neoplastic cells.

14 Claims, No Drawings

STILBENE DERIVATIVES

BACKGROUND OF THE INVENTION

1. Field of the Invention

Some chondrogenetic disorders and dermatological disorders such as psoriasis and malignant disorders such as leukemia can be looked upon as a disease involving a block or an abnormality in differentiation. The present invention relates to novel organic compounds which have great potential as useful medicaments and which may accordingly be developed and offered for treating the disorders of humans and animals.

Further the compounds of the prevent invention can be used for diagnosis of leukemia.

The present invention relates to novel organic compounds which have great potential as useful medicaments and which may accordingly be developed and offered for therapeutical use in the field of cancer chemotherapy.

2. Description of the Prior Art

It is already known that an interesting method exists, by which the differentiation of cancer cells is effected and an extinction of cancer cells caused to occur (J. Med. Chem. 25 1269–1277 (1982) with Title: Retinoids at the Threshold: Their Biological Significance and Therapeutic Potential; Cancer Research (Suppl.) 43 2469s–2475s May 1983 with Title: Inhibition of Carcinogenesis by Retinoids; BLOOD of J.A.S. of Hematology 62 709–721 (1983) with Title: Induction of Differentiation of Human Acute Myelogenous Leukemia Cell; Therapeutic Implications; Experientia 34 1105–1246 1978: with Title: Retinoids, a new class of compounds with prophylactic and therapeutic activities in oncology and dermatology and Cell Technology 2, No. 12 (1983)). This literature reports also that retinoic acid, retinoids, and related compounds have significant therapeutic potential in oncology and dermatology.

In the specification of DOS No. 28 54 354, it is reported that stilbene derivatives such as p-((E)-2-(5,6,7,8-tetrahydro-5,5,8,8-tetramethyl-2-naphthyl)propenyl)-benzylmethyl ether are pharmacologically valuable and useful for systemic and topical treatment and prophylaxis of benign or malignant tumors. These compounds and retinoids are said to be suitable for systemic and topical treatment of acne, psoriasis and precancerous conditions and for other dermatopathy which is accompanied by hyperkeratinization as well other pathologic and allergic dermatological disease.

DETAILED DESCRIPTION OF THE INVENTION

It has now been found that the compounds of the formula (I):

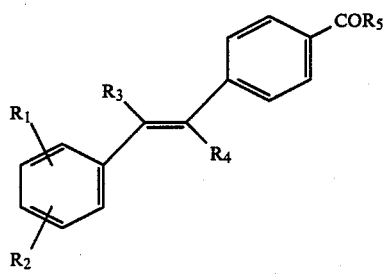

wherein $R_1$ and $R_2$ each independently represents hydrogen, lower alkyl, or cycloalkyl, with the proviso that both $R_1$ and $R_2$ cannot be hydrogen simultaneously, $R_3$ and $R_4$ represent hydrogen, methyl, or trifluoromethyl, and $R_5$ represents hydroxyl, lower alkoxyl, lower alkylamino of the formula $-NR_6R_7$ (wherein $R_6$ and $R_7$ represent hydrogen or lower alkyl), are capable of inducing the differentiation of malignant cells, especially leukemia cells, both morphologically and functionally, and can therefore be used in the therapy of malignant diseases in accord with the aforesaid third method.

By the term "lower" in formula I is meant a straight or branched carbon chain having 1–6 carbon atoms. Therefore, the lower alkyl moiety of the lower alkyl, lower alkoxy, and lower alkylamino group encompassed by $R_1$, $R_2$, $R_5$, $R_6$ and $R_7$ is representatively methyl, ethyl, propyl, isopropyl, butyl, sec-butyl, tert-butyl, etc. The lower alkoxy moiety of the lower alkoxy group is representatively methoxy, ethoxy, propoxy, butoxy, etc., and the lower alkylamino group is representatively mono- or dimethylamino, mono- or diethylamino, etc.

By cycloalkyl there is representatively intended cyclopropyl, cyclobutyl, methylcyclopropyl, and the like.

Moreover, the compounds of this invention may be of either or both of the trans and cis types.

The compounds of above-shown general formula I provided by this invention form salts with bases. This invention includes the pharmaceutically-acceptable salts of the compounds of general formula I, and examples of these salts are the salts with alkali metals such as sodium, potassium, etc., or alkaline earth metals such as calcium, etc.; the salts with ammonia; and the salts with organic bases such as methylamine, ethylamine, diethylamine, trimethylamine, triethylamine, pyridine, picoline, arginine, lysine, etc.

The compounds of this invention have been tested according to established test procedure which shows the differentiation of malignant cells, whereby the differentiation of human acute promyelocytic leukemia cells (HL-60) and their conversion to granulocytes (myelocytes) can be assayed by an observation of the morphological changes of nuclei and by the measurement of the degree of reduction of nitro-blue tetrazolium (NBT) which is induced by a test compound (Proc. Natl. Acad. Sci. USA 77, 2936–2940 (1980) with Title: Induction of differentiation of the human promyelocytic leukemia cell line (HL-60) by retinoic acid).

The HL-60 cell are cultured in plastic flasks in RPMI-1640 medium supplemented with 5% heat inactivated fetal calf serum and antibiotics (penicillin G and streptomycin). The cells ($3 \times 10^4$/ml) were cultured with a compound of the present invention for 4 days. Growth inhibition of the cells by the test compounds was determined by counting the number of cells by microscope and relative ratio was examined by taking the number of cells by control (without test compound) as 100%. The cells are fixed and stained with Wright-Giemsa to examine the morphological changes of the nuclei.

The cells treated with the present compounds are differentiated to mature granulocytes (myelocytes, metamyelocytes and neutrophiles), just as the cells treated with retinoic acid.

The biochemical activity of cells treated with the compound was measured as follows:

The cells after 5 days incubation are centrifuged and diluted with RPMI-1640 medium supplemented with 5% fetal calf serum, to provide a definite number of the cells. To the diluted cell suspension are then added 200 ng/ml of 12-o-tetradodecanoylphorbol-13-acetate (TPA), and the resulting culture medium is then incubated for 20 minutes at 37° C. in the presence of 0.1% of NBT. Thus, the mature differentiated cells containing blue-black formazan is counted by microscopy, so that the ratio of the cells having the ability to reduce NBT, to total cells, can be calculated.

The cells treated with the compound of this invention show the NBT reduction activity which corresponds to the important biochemical activity of differentiated cells.

The results of the tests according to the above-mentioned methods are summarized in Table 2.

As can be seen from the results shown in Table 2 the activity of the compounds of this invention is observed at a concentration below $10^{-6}$ Mol. Those compounds, wherein $R_1$ and $R_2$ are both ethyl, isopropyl or t-butyl, or wherein $R_1$ or $R_2$ at the meta position is t-butyl, are most active and indeed at concentrations between $10^{-8}$ and $10^{-9}$.

The alkyl-substitution $R_1$ and $R_2$ on the phenyl group in the formula (I) is a characteristic of the stilbene-4-carboxylic acids and their derivatives which are the compounds of this invention. Such a compound, wherein the alkyl group is a middle alkyl group, especially wherein $R_1$ is an isopropyl, cyclopropyl, cyclobutyl, or butyl group, or wherein $R_1$ and $R_2$ are both an ethyl, isopropyl or tert-butyl group, is effective. On the other hand such a compound, wherein $R_1$ and $R_2$ are both hydrogen, does not exhibit the desired activity.

The compounds of the formula (I), wherein $R_3$ and $R_4$ represent hydrogen, methyl, or trifluoromethyl, are especially effective.

Since the compounds of the present invention differentiate the leukemia cells to mature granulocytes morphologically and functionally and inhibit the cells-growth potentially, those can be used as medicines to use for treatment of humans and animals with cancer and dermatological disorders, and further as diagnosis for determining the type of leukemia by a measuring method, whereby the blood of a patient with leukemia is incubated in vitro in the presence of a present compound in an Onalogious manner as described in the morphological assay for the HL-60 cells: Only promyelocytic leukemia cells, but not lymphocytic leukemia cells, differentiate to mature granulocytes which can be clearly determined by microscope (See: Saibo (Cells) 14 533 (1982)).

When the incubation is performed in a soft agar, promyelocytic leukemia cells do not form a colony, since the differentiated cells do not proliferate further.

Thus, these compounds are very useful in the determination of promyelocytic leukemia, which enables one to select the therapeutical methods.

These compounds suppress the hyperkera keratinization of human tissue cells, and are useful for the treatment of cystic acne, psoriasis and related cutaneous disorders of keratinization and of epithelial differentiation.

The medical compositions containing the compounds of this invention as the main component are formulated by a conventional manner using conventional carriers for formulation and excipients. The medicaments may be administered orally as tablets, pills, capsules, granules, etc., or may be administered parenterally as injections such as intraveous injections, intramuscular injections, etc., in the form of an ointment, cream, and the like for external application or as aerosols, suppositories, etc. The doses of the medicaments are properly determined according to each case on considering the symptom, the age of patient, sex distinction, etc., but are usually 1–100 mg per day for adult in case of oral administration and 1–50 mg per day for adult in case of parenteral administration, which is administered in 2–3 times a day.

The stilbene derivatives represented by the formula (I)

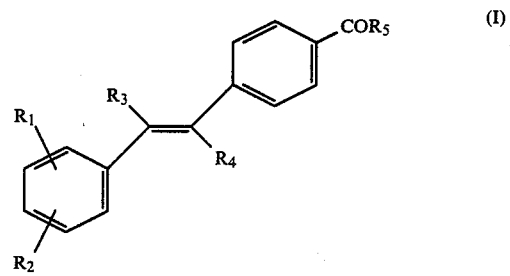

wherein $R_1$ and $R_2$ each independently represents hydrogen, lower alkyl, or cycloalkyl, with the proviso that both cannot be hydrogen simultaneously, $R_3$ and $R_4$ represent hydrogen, methyl, or trifluormethyl, and $R_5$ represents hydroxyl, lower alkoxyl, or a group of the formula $-NR_6R_7$ (wherein $R_6$ and $R_7$ are hydrogen or lower alkyl), can be prepared by the reaction of a compound represented by the formula (II)

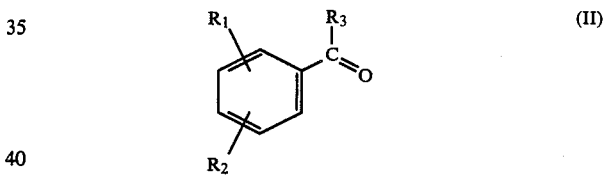

wherein $R_1$, $R_2$ and $R_3$ have the same meanings as given previously, with a compound represented by the formula (III)

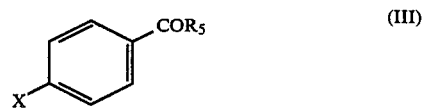

wherein $R_5$ has the same meaning as presiously assigned and X represents a group having the formula:

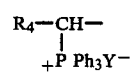

(wherein $R_4$ has the meaning previously assigned and Y is the anion of an organic or inorganic acid) or a dialkoxyphosphonylalkyl group having the formula:

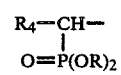

(wherein $R_4$ has the meaning previously given and R represents a lower alkyl group) and, if necessary or desirable, converting the carboxylic acid ester group represented by the formula —COR₅ into the carboxylic acid group or the carbamide group.

The following examples are given by way of illustration only and are not to be construed as limitations of this invention.

EXAMPLE 1

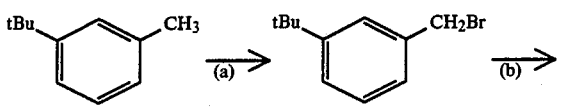

Step (a) Bromination of butyltoluene

A solution of 400 mg (2.7 mmole) of m-tert. butyltoluene, 540 mg (3.03 mmole) of N-bromsuccinic imide and 50 mg of azoisobutylnitrile in 10 ml of chloroform was heated under reflux for 2 hours. After completion of the reaction, the insoluble substances were removed by filtration and the solvent was distilled off to give the bromide (yield: 98%).

Step (b)

640 mg (2.82 mmole) of m-tert.-butylbenzylbromide obtained in Step (a) and 660 mg (2.52 mmole) of triphenylphosphine were disolved in 7 ml of benzene and the resulting solution was heated under reflux for 5 hours. After completion of the reaction, the precipitated crystals were removed by filtration to give the phosphonium bromide (yield: 68.2%).

Step (c) Wittig Reaction

To a solution of 634 mg (1.29 mmole) of phosphoniumbromide and 216 mg (1.32 mmole) of terephthalaldehyde methyl ester in 15 ml of anhydrous methanol was added 80 mg (1.48 mmole) of sodium methylate, and the resulting mixture was stirred at room temperature for one night. The precipitate (trans form) was removed by filtration. Further, by chromatography of the filtrate containing both the trans and cis forms, further compound in the trans form was be obtained (yield 50%).

Step (d) Hydrolysis

To a solution of 50 mg (0.16 mmole) of methylester obtained in Step (c) in 3 ml ethanol was added 5 ml of 1N-sodium hydroxide and the resulting solution heated under reflux for 2 hours. After completion of the reaction, the solution was rendered acidic with dilute aqueous hydrochloric acid solution and extracted with ethyl acetate. The ethyl acetate layer was washed with water until the pH of the washings reached 7, dried over anhydrous sodium sulfate, and solvent distilled off to give the carboxylic acid having a melting point of >300° C. (yield 98%).

Elemental Analysis for $C_{19}H_{20}O_2$: Calcd. C; 81.39, H; 7.19, Found C; 81.32, H; 7.20.

EXAMPLE 2

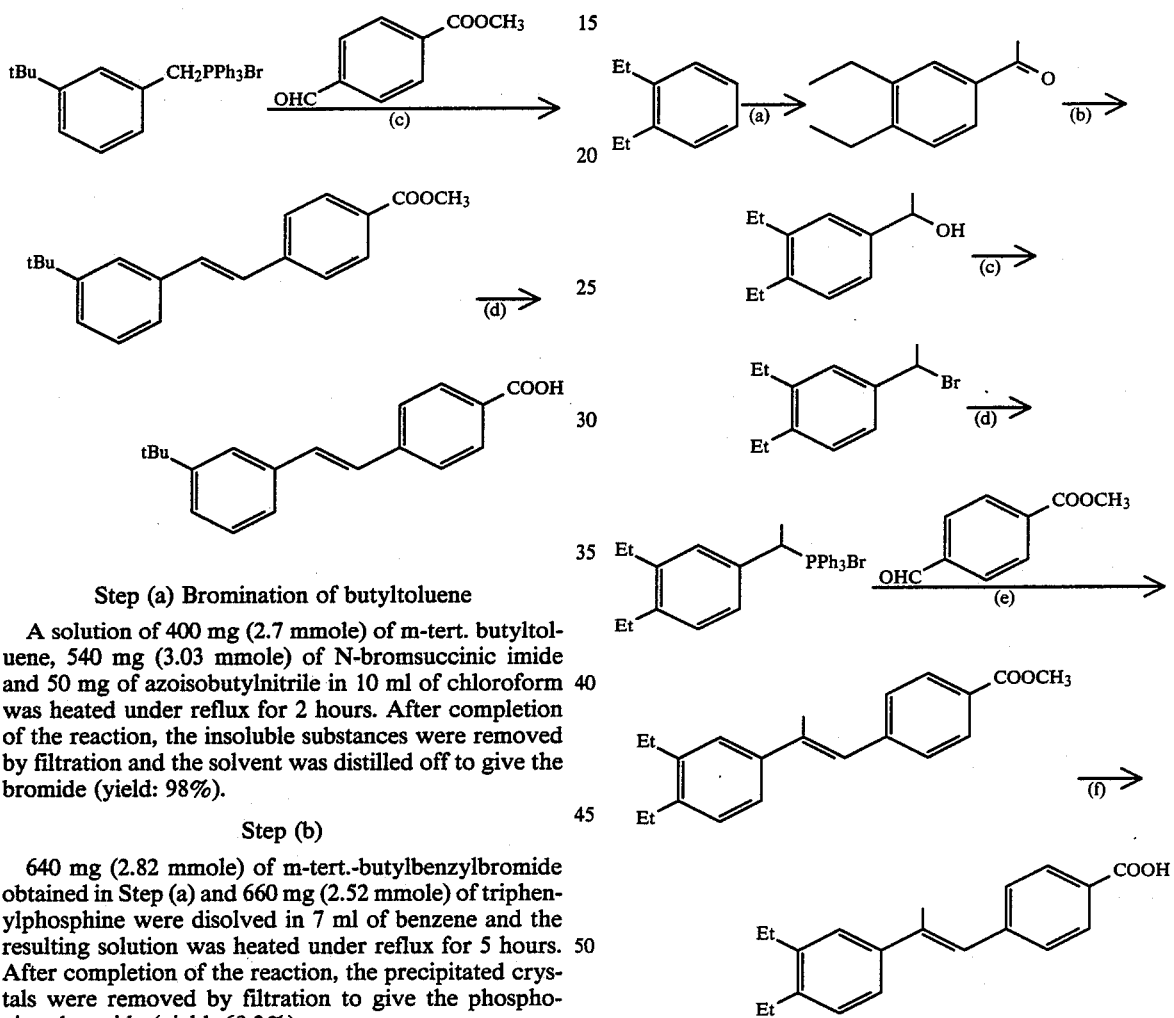

Step (a) Acetylation by Friedel-Craft

To a suspension of 5.0 g (37.3 mmole) of o-diethylbenzene and 3.2 g (40.7 mmole) of acetyl chloride in 30 ml of 1,2-dichlorethane was slowly added 5.7 g (42.7 mmole) of aluminum chloride at a temperature of 0° C. After the addition was complete, the mixture was stirred additionally for one hour. After completion of the reaction, the reaction product was poured over ice and extracted with ether.

The resulting organic layer was washed successively by with 1N-sodium bicarbonate, water, saturated aqueous saline solution, and dried over anhydrous sodium sulfate.

The solvent was removed to yield the acetyl product (yield 62.1%), which was purified by distillation to give the pure product having a boiling point of 110°–112.5° C./2.5 mmHg.

Step (b) Reduction

To a solution of 4.08 g (23.1 mmole) of 3,4-diethylacetophenone in 15 ml of methanol was slowly added 570 mg (15.1 mmole) of sodium borohydride at a temperature of 0° C.

After addition was complete, the mixture was stirred for 1.5 hours. After completion of the reaction, the reaction product was poured over a mixture of ice and dilute aqueous hydrochloric acid solution and extracted with ether. The ether layer was washed successively with 1N sodium bicarbonate, water, and aqueous saline solution and dried over anhydrous sodium sulfate. The solvent was distilled off to yield the alcohol product (yield 86.3%), which was purified by distillation to give the pure product having a boiling point of 114°–115° C./2.5 mmHg.

Step (c) Bromination

To a mixture of 3 ml of ether and 30 ml of hexane was added with stirring 3.56 g (19.9 mmole) of the alcohol product obtained in Step (b) and 2 drops of pyridine. To the resulting solution was slowly added a solution of 1.05 ml of phosphorus tribromide in 10 ml of hexane at temperature of 0° C. After the addition was complete, the solution was stirred additionally for 1.5 hours. After the reaction was complete, the reaction product was poured over ice and extracted with ether. The organic layer was washed successively with 1N-sodium bicarbonate, water and aqueous saline solution, dried over sodium sulfate, and the solvent distilled off at low temperature to give the bromide product (yield 95.8%), which was used in the following Step (d) without purification.

Step (d)

A solution of 4.612 g (19.1 mmole) of the bromide product and 4.993 g (19.0 mmole) of triphenylphosphine in 30 ml of benzene was heated under reflux for 24 hours. After the reaction was complete, the reaction solution was allowed to cool to room temperature. The precipitate was isolated by filtration. Concentration of the filtrate and chromatography through a silica gel column gave further phosphonium bromide (yield 64.7%).

Step (e) Wittig Reaction

A solution of 4.8 g (9.53 mmole) of the phosphonium bromide and 1.56 g (9.51 mmole) of terephthalaldehyde acid methyl ester in 40 ml butylene oxide was heated in a stream of argon under reflux for 24 hours. After the reaction was complete, the reaction solution was concentrated. Chromatography on a silica gel column and recrystallization gave the methyl ester product in the trans form having a melting point of 50°–50.5° C. (yield 71%).

Step (f) Hydrolysis

To a solution of 98 mg (0.29 mmole) of the methylester obtained in Step (e) in 5 ml of ethanol was added 5 ml of 1N sodium hydroxide and the resulting solution was heated under reflux for two hours. After reaction was complete, the solution was rendered acidic with dilute aqueous hydrochloric acid solution and extracted with ethyl acetate. The ethyl acetate layer was washed with water, until the pH of the washings reached 7, and dried over anhydrous sodium sulfate. The solvent was removed to give the carboxylic acid having a melting point of 193°–193.5° C. (yield 95%).

Elemental Analysis for $C_{20}H_{22}O_2$: Calcd.: C; 81.60, H; 7.53, Found: C; 81.59, H; 7.64.

EXAMPLE 3

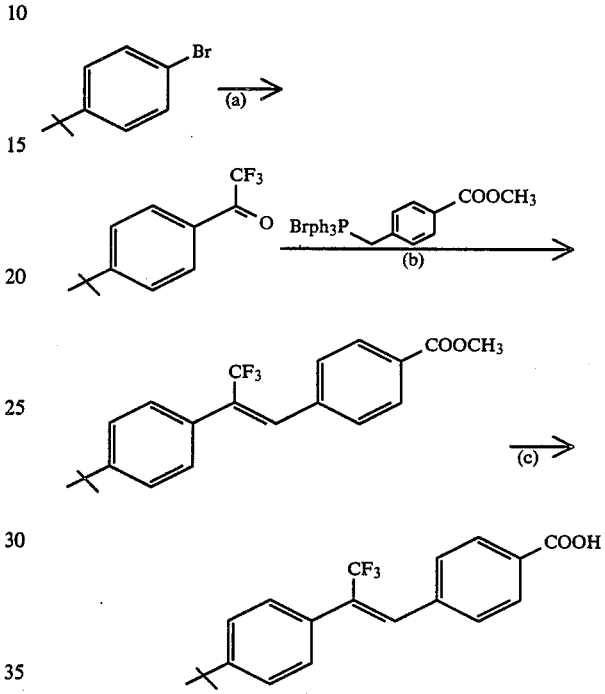

Step (a) Trifluoroacetylation

To a mixture of 5.0 g t-butylbromobenzene (23.5 mmole) with 50 ml of dried ether was added 570 mg metallic magnesium (23.5 mmole), and the resulting mixture was heated in a stream of argon under reflux for 30 minutes.

To the reaction mixture was slowly added 0.6 ml trifluoroacetylchloride under ice-cooling. After the addition was complete, the reaction mixture was heated under reflux for two hours, poured over ice, and extracted with ether. The ether layer was washed successively with 1N sodium bicarbonate, water, saturated aqueous saline solution, and dried over anhydrous sodium sulfate. Distillation and chromatography through a silica gel column gave the desired product (yield 20.0%).

Step (b) Wittig Reaction

A suspension of 15 mg (0.04 mmole) of 18-crown-6 ether and 500 mg of (8.61 mmole) of potassium fluoride (anhydride) in 5 ml of anhydrous acetonitrile was stirred for 20 minutes at room temperature in a stream of argon. The reaction solution was heated at 70° to 80° C. and a suspension of 100 mg of p-tert.-butyl $\alpha,\alpha,\alpha$-trifluoroacetophenone and 213 mg of phosphonium salt (prepared from 4-bromomethylbenzoic acid methyl ester and triphenylphosphine) in acetonitrile was added thereto all at one time. Then, 2–3 hours after addition, the reaction solution was filtered and concentrated to give a mixture of the desired methyl ester compound in trans and cis forms (yield 88.3%, trans/cis=1:7). Silica gel chromatography gave the pure trans compound (yield 10%).

Step (c) Hydrolysis

To a solution of 40 mg (0.11 mmole) of the methyl ester in 2 ml of ethanol was added 3 ml of 1N sodium hydroxide under reflux over a period of two hours. After reaction was complete, the reaction mixture was acidified with dilute aqueous hydrochloric acid solution and extracted with ethyl acetate. The ethyl acetate layer was washed with water until the pH of the washings reached 7, and dried over anhydrous sodium sulfate. The solvent was removed to give the carboxylic acid having a melting point of 182°–183° C. (yield 69.4%). MASS: M+ 348 (calcd. $C_{20}H_{19}F_3O_2=348$)

As described in the foregoing Examples 1-3, further compounds of Table I have been prepared. In the column of synthesis in Table I is stated the number of the corresponding Example, according to which each compound is prepared.

TABLE 1

| | $R_1$ | $R_2$ | $R_3$ | $R_5$ | mp | Anal | synthesis |
|---|---|---|---|---|---|---|---|
| 1 | $CH_3$ | $CH_3$ | $CH_3$ | $CH_3$ | 93–94 | $C_{19}H_{20}O_2$ | 2 |
| 2 | " | " | " | H | 213–215 | $C_{18}H_{18}O_2$ | 2 |
| 3 | $C_2H_5$ | $C_2H_5$ | " | $CH_3$ | 50–50.5 | $C_{21}H_{24}O_2$ | 2 |
| 4 | " | " | " | H | 193–194.5 | $C_{20}H_{22}O_2$ | 2 |
| 5 | $isoC_3H_7$ | $isoC_3H_7$ | " | H | 236.5–237 | $C_{22}H_{26}O_2$ | 2 |
| 6 | t-Bu | H | H | H | >300 | $C_{19}H_{20}O_2$ | 1 |
| 7 | H | t-Bu | H | H | 213.5–215 | $C_{19}H_{20}O_2$ | 1 |
| 8 | " | " | " | $CH_3$ | 104.5–105 | $C_{21}H_{24}O_2$ | 2 |
| 9 | " | " | $CH_3$ | H | 243–244.5 | $C_{20}H_{22}O_2$ | 2 |
| 10 | " | " | $CF_3$ | H | 182–183 | M+348 | 3 |
| 11 | $C_3H_5$ | H | $CH_3$ | H | 210–220 | $C_{19}H_{18}O_2$ | 2 |

TABLE 2

| Compound (No.) | Concent. (M) | Promyelocytes (%) | Myelocytes and Metamyelocytes (%) | Banded and Segmented neutrophils (%) | Reductivity of NBT (%) | Growth inhibition of cells (%) |
|---|---|---|---|---|---|---|
| Blank | — | 98 | 2 | 0 | 0 | 100 |
| Retinoic acid | $10^{-7}$ | 25 | 71 | 4 | 75 | 32 |
| 1 | $10^{-6}$ | 90 | 10 | 0 | 5 | 92 |
| 2 | $10^{-6}$ | 81 | 18 | 1 | 8 | 78 |
| 3 | $10^{-9}$ | 40 | 53 | 7 | 40 | 65 |
| 4 | $10^{-9}$ | 27 | 58 | 15 | 76 | 30 |
| 5 | $10^{-9}$ | 35 | 58 | 8 | 76 | 18 |
| 6 | $10^{-8}$ | 46 | 31 | 3 | 56 | 21 |
| 7 | $10^{-6}$ | 80 | 19 | 1 | 11 | 31 |
| 8 | $10^{-7}$ | 60 | 34 | 6 | 15 | 33 |
| 9 | $10^{-7}$ | 66 | 32 | 2 | 11 | 33 |
| 10 | $10^{-7}$ | 90 | 10 | 0 | 2 | 70 |
| 11 | $10^{-8}$ | 40 | 52 | 8 | 61 | 29 |

What is claimed is:

1. A stilbene compound represented by the formula (I):

wherein $R_1$ and $R_2$ each independently represents hydrogen, lower alkyl, or cycloalkyl, with the proviso that both $R_1$ and $R_2$ cannot be hydrogen simultaneously, $R_3$ and $R_4$ independently represent hydrogen, methyl, or trifluoromethyl, and $R_5$ represents hydroxyl, lower alkoxyl, or lower alkylamino of the formula $-NR_6R_7$, wherein $R_6$ and $R_7$ each independently represents hydrogen or lower alkyl.

2. A compound according to claim 1, wherein $R_1$ represents isopropyl, cyclopropyl, or butyl.

3. A compound according to claim 1, wherein $R_1$ and $R_2$ each represents ethyl or isopropyl.

4. A compound according to claim 1, wherein $R_3$ and $R_4$ each represents hydrogen, methyl, or trifluoromethyl.

5. A compound of claim 1 which is [E-2-(3,4-di-isopropylphenyl)propenyl]benzoic acid.

6. A compound of claim 1 which is [E-2-(3-tert.-butylphenyl)ethenyl]benzoic acid.

7. Method for diagnosis to determine the type of leukemia which comprises the incubation of the blood of a patient with leukemia in vitro in the presence of a compound of claim 1, and the observation of morphological changes and/or of colony formation of the leukemia cell.

8. Use of one or more stilbene derivatives of claim 1 as medicaments for treatment of dermatological disorders of humans and animals.

9. A differentiation-inducing agent for neoplastic cells, especially leukemia cells, comprising as active ingredient one or more stilbene compounds of claim 1.

10. A compound of claim 1, which is [E-2-(4-tert.-butylphenyl)-3,3,3-trifluoropropenyl]-benzoic acid.

11. A compound of claim 1 which is [E-2-(3-cyclopropyl-phenyl)-ethenyl]benzoic acid.

12. A process for preparation of a stilbene represented by the formula (I):

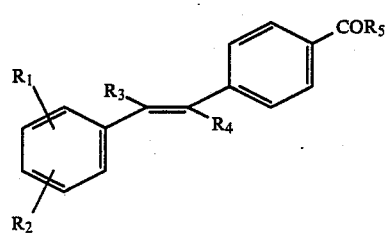

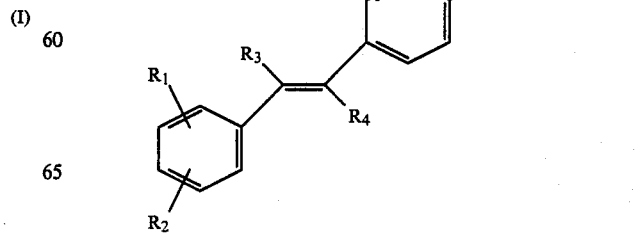

wherein $R_1$ and $R_2$ each independently represents hydrogen, lower alkyl or cycloalkyl, with the proviso that both $R_1$ and $R_2$ cannot be hydrogen simultaneously, $R_3$ and $R_4$ independently represent hydrogen, methyl, or trifluoromethyl, and $R_5$ represents hydroxyl, lower alkoxyl, or lower alkylamino of the formula $-NR_6R_7$, wherein $R_6$ and $R_7$ each independently represents hydrogen or lower alkyl, which comprises reacting a compound represented by the formula (II)

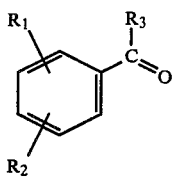
(II)

wherein $R_1$, $R_2$ and $R_3$ have the meanings previously assigned, with a compound represented by the formula (III)

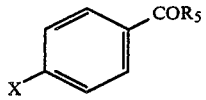
(III)

wherein $R_5$ has the meaning previously assigned and X represents a group represented by the formula:

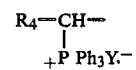

wherein $R_4$ has the meaning previously assigned and Y is an anion of an organic or inorganic acid or a dialkoxyphosphonylalkyl group represented by the formula:

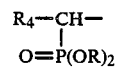

wherein $R_4$ has the value previously assigned and R represents a lower alkyl group and, if desired, converting the carboxylic acid ester group represented by the formula $-COR_5$ into the carboxylic acid group or a carbamide group.

13. Compound of claim 1 which is [E-2-(3,4-diethylphenyl)propenyl]benzoic acid.

14. Compound of claim 1 which is [E-2-(3,4-diethylphenyl)propenyl]benzoic acid methyl ester.

* * * * *

UNITED STATES PATENT AND TRADEMARK OFFICE
CERTIFICATE OF CORRECTION

PATENT NO. : 4,723,028
DATED : February 2, 1988
INVENTOR(S) : Koichi Shudo

It is certified that error appears in the above—identified patent and that said Letters Patent is hereby corrected as shown below:

Title Page, [56] References Cited, OTHER PUBLICATIONS, line 1; "Chemica" should be changed to -- Eur. J. Med. Chem. — Chimica --
Title Page, [56] References Cited, OTHER PUBLICATIONS, line 13; "1269, 1277," should read -- 1269-1277, --
Title Page, [56] References Cited, OTHER PUBLICATIONS, line 18; after "Koeffler" insert -- H. --
Col. 2, line 50; "cell" should read -- cells --
Col. 4, line 28; "trifluormethyl," should read -- trifluoromethyl, --
Col. 4, line 52; "presiously" should read -- previously --
Col. 5, line 4; after "way" insert -- of --
Col. 5, line 49; "disolved" should read -- dissolved --
Col. 5, line 64; "was be obtained" should read -- was obtained --
Col. 6, line 59; "1,2-dichlorethane" should read -- 1,2-dichloroethane --

Signed and Sealed this

Thirteenth Day of September, 1988

*Attest:*

DONALD J. QUIGG

*Attesting Officer*     *Commissioner of Patents and Trademarks*

Notice of Adverse Decisions in Inteference

In Interference No. 102,170, involving Patent No. 4,723,028, K. Shudo, STILBENE DERIVITIVES, final judgment adverse to the patentee was rendered December 11, 1989, as to claims 1-6, 8-11, 13 and 14.

*(Official Gazette February 20, 1990)*